US011433383B2

(12) United States Patent
Aiki et al.

(10) Patent No.: US 11,433,383 B2
(45) Date of Patent: Sep. 6, 2022

(54) METHOD FOR PRODUCING AMMOXIDATION CATALYST AND METHOD FOR PRODUCING ACRYLONITRTIE

(71) Applicant: ASAHI KASEI KABUSHIKI KAISHA, Tokyo (JP)

(72) Inventors: Shota Aiki, Tokyo (JP); Akiyoshi Fukuzawa, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 676 days.

(21) Appl. No.: 16/307,280

(22) PCT Filed: Jun. 9, 2017

(86) PCT No.: PCT/JP2017/021543
§ 371 (c)(1),
(2) Date: Dec. 5, 2018

(87) PCT Pub. No.: WO2017/217343
PCT Pub. Date: Dec. 21, 2017

(65) Prior Publication Data
US 2019/0126262 A1   May 2, 2019

(30) Foreign Application Priority Data

Jun. 14, 2016 (JP) .............................. JP2016-118186

(51) Int. Cl.
| | | |
|---|---|---|
| B01J 35/00 | (2006.01) | |
| B01J 37/00 | (2006.01) | |
| B01J 37/04 | (2006.01) | |
| B01J 37/08 | (2006.01) | |
| C07C 253/26 | (2006.01) | |
| C07C 255/08 | (2006.01) | |
| B01J 23/887 | (2006.01) | |
| B01J 23/883 | (2006.01) | |
| B01J 23/881 | (2006.01) | |
| C07B 61/00 | (2006.01) | |

(52) U.S. Cl.
CPC ......... *B01J 37/0045* (2013.01); *B01J 23/881* (2013.01); *B01J 23/883* (2013.01); *B01J 23/8872* (2013.01); *B01J 23/8876* (2013.01); *B01J 37/00* (2013.01); *B01J 37/0018* (2013.01); *B01J 37/04* (2013.01); *B01J 37/08* (2013.01); *B01J 37/088* (2013.01); *C07C 253/26* (2013.01); *C07C 255/08* (2013.01); *B01J 2523/00* (2013.01); *B01J 2523/54* (2013.01); *B01J 2523/68* (2013.01); *B01J 2523/842* (2013.01); *C07B 61/00* (2013.01); *Y02P 20/52* (2015.11)

(58) Field of Classification Search
CPC .... B01J 37/0045; B01J 23/881; B01J 23/883; B01J 23/8872; B01J 23/8876; B01J 37/00; B01J 37/0018; B01J 37/04; B01J 37/08; B01J 37/088; C07C 253/26; C07C 255/08

See application file for complete search history.

(56) References Cited

U.S. PATENT DOCUMENTS

| | | | |
|---|---|---|---|
| 4,264,476 A | 4/1981 | Umemura et al. | |
| 5,059,573 A | 10/1991 | Sasaki et al. | |
| 6,479,691 B1 | 11/2002 | Sasaki et al. | |
| 6,610,629 B2 * | 8/2003 | Hinago ................. | C07C 51/215 502/300 |
| 2009/0030230 A1 | 1/2009 | Fischer et al. | |
| 2009/0270648 A1 | 10/2009 | Yanagita et al. | |
| 2014/0171303 A1 | 6/2014 | Yoshida et al. | |
| 2015/0238939 A1 | 8/2015 | Yoshida et al. | |

FOREIGN PATENT DOCUMENTS

| | | |
|---|---|---|
| EP | 3409356 A1 | 12/2018 |
| EP | 3409357 A | 12/2018 |
| EP | 3450018 A1 | 3/2019 |
| JP | 55-056839 A | 4/1980 |
| JP | 2-214543 A | 8/1990 |
| JP | 2000-005603 A | 1/2000 |
| JP | 2006-61888 A | 3/2006 |
| JP | 2008-212779 A | 9/2008 |
| JP | 2008-237963 A | 10/2008 |
| JP | 2009-511256 A | 3/2009 |
| JP | 2009-285581 A | 12/2009 |
| JP | 2013-017917 A | 1/2013 |
| JP | 2013-527141 A | 6/2013 |
| JP | 2013-169482 A | 9/2013 |
| JP | 2015-188802 A | 11/2015 |
| JP | 2016-055271 A | 4/2016 |
| RU | 2575346 C2 | 2/2016 |
| WO | WO 2008/050767 A1 | 5/2008 |
| WO | WO 2011/119203 A1 | 9/2011 |
| WO | WO 2012/063771 A1 | 5/2012 |
| WO | WO 2014/051090 A1 | 4/2014 |

OTHER PUBLICATIONS

Extended European Search Report, dated Apr. 29, 2019, for European Application No. 17813240.3.
International Preliminary Report on Patentability and Written Opinion of the Internatibnal Searching Authority(Forms PCT/IB/326, PCT/IB/373 and PCT/ISA/237), dated Dec. 27, 2018, for International Application No. PCT/JP2017/021543, with an English Translation of the Written Opinion.
International Search Report (PCT/ISA/210) issued in PCT/JP2017/021543, dated Sep. 12, 2017.

* cited by examiner

*Primary Examiner* — James A Fiorito
(74) *Attorney, Agent, or Firm* — Birch, Stewart, Kolasch & Birch, LLP

(57) ABSTRACT

A method for producing an ammoxidation catalyst, the method including: a step (i) of preparing a starting material slurry comprising molybdenum, bismuth, iron, and a carboxylic acid compound; a step (ii) of stirring the starting material slurry in a temperature range of 30 to 50° C. for 20 minutes to 8 hours, thereby preparing a precursor slurry; a step of spray-drying the precursor slurry, thereby obtaining a dried particle; and a step of calcining the dried particle.

3 Claims, No Drawings

METHOD FOR PRODUCING AMMOXIDATION CATALYST AND METHOD FOR PRODUCING ACRYLONITRTIE

TECHNICAL FIELD

The present invention relates to a method for producing an ammoxidation catalyst and a method for producing acrylonitrile.

BACKGROUND ART

A reaction for producing acrylonitrile by reacting propylene with ammonia in the presence of molecular oxygen is known as "ammoxidation reaction", and this reaction is used as a method for industrially producing acrylonitrile.

In this reaction, an oxide catalyst is utilized for achieving a favorable acrylonitrile yield. For example, a catalyst containing Mo—Bi—Fe or Fe—Sb as essential components is industrially used. Catalysts obtained by adding additional elements to the above-described essential components, in order to achieve a further favorable acrylonitrile yield, are also known (see, for example, Patent Literatures 1 and 2).

On the other hand, attempts to improve the acrylonitrile yield by not only improving a metal composition but also improving a catalyst preparation step have also been made. For example, Patent Literature 3 describes a method for preparing an ammoxidation catalyst containing molybdenum, bismuth, and iron as essential components, in which a coordinating organic compound is added to a starting material slurry.

Patent Literature 4 describes a method for producing a catalyst for producing acrylonitrile, the method including adjusting a temperature of a slurry containing molybdenum, bismuth, iron, tungsten, and the like within the range of 30 to 70° C.

CITATION LIST

Patent Literature

Patent Literature 1: Japanese Patent Laid-Open No. 2013-169482
Patent Literature 2: Japanese Patent Laid-Open No. 2008-212779
Patent Literature 3: Japanese Patent Laid-Open No. 2013-17917
Patent Literature 4: Japanese Patent Laid-Open No. 2008-237963

SUMMARY OF INVENTION

Technical Problem

The catalyst prepared by the method described in Patent Literature 3 greatly improves acrylonitrile selectivity, but the catalyst is worn when industrially used as a fluidized bed catalyst over a long period of time, and the acrylonitrile yield and the fluidity of the catalyst may be worsened in some cases. In addition, the catalyst described in Patent Literature 4 worsens the dispersibility of metal components only to lower the acrylonitrile yield because a carboxylic acid is not added to the slurry. As described above, an ammoxidation catalyst exhibiting a high acrylonitrile yield and having attrition strength to endure long-term use as a fluidized bed catalyst cannot be obtained by the catalyst production techniques described in Patent Literatures 1 to 4.

The present invention has been completed in consideration of the problems, and an object of the present invention is to provide a method for producing an ammoxidation catalyst exhibiting a high acrylonitrile yield and having attrition strength to endure long-term use as a fluidized bed catalyst and a method for producing acrylonitrile.

Solution to Problem

The present inventors have conducted studies to solve the problems to find that the problems can be solved by adjusting within a specific range the conditions relating to the temperature and the stirring time during producing a catalyst, thereby completed the present invention.

That is, the present invention is as follows.

[1]

A method for producing an ammoxidation catalyst, the method comprising:

a step (i) of preparing a starting material slurry comprising molybdenum, bismuth, iron, and a carboxylic acid compound;

a step (ii) of stirring the starting material slurry in a temperature range of 30 to 50° C. for 20 minutes to 8 hours, thereby preparing a precursor slurry;

a step of spray-drying the precursor slurry, thereby obtaining a dried particle; and a step of calcining the dried particle.

[2]

The method for producing the ammoxidation catalyst according to [1], wherein the precursor slurry has a viscosity of 1 to 100 cp.

[3]

The method for producing the ammoxidation catalyst according to [1] or [2], wherein the ammoxidation catalyst has a composition represented by the following formula (1):

$$Mo_{12}Bi_aFe_bX_cY_dZ_eO_f \quad (1);$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; provided that a proportion of cobalt is 20 atomic % or more and/or a proportion of magnesium is 20 atomic % or less in the element X; a, b, c, d, and e satisfy $0.1 \leq a \leq 2.0$, $0.1 \leq b \leq 3.0$, $0.1 \leq c \leq 10.0$, $0.1 \leq d \leq 3.0$ and $0.01 \leq e \leq 2.0$, respectively; and f represents a number of oxygen atoms needed to satisfy atomic valence requirements of other elements present therein.

[4]

The method for producing the ammoxidation catalyst according to any of [1] to [3], wherein a content of the carboxylic acid compound in the precursor slurry is 0.01 to 0.10 mol equivalents based on a sum of metal elements constituting the ammoxidation catalyst.

[5]

A method for producing acrylonitrile by reacting propylene, molecular oxygen, and ammonia, wherein the ammoxidation catalyst produced by the method according to any of [1] to [4] is used.

[6]

A method for producing acrylonitrile, the method comprising:
a step (i) of preparing a starting material slurry comprising molybdenum, bismuth, iron, and a carboxylic acid compound;
a step (ii) of stirring the starting material slurry in a temperature range of 30 to 50° C. for 20 minutes to 8 hours, thereby preparing a precursor slurry;
a step of spray-drying the precursor slurry, thereby obtaining a dried particle;
a step of calcining the dried particle, thereby obtaining an ammoxidation catalyst; and
a step of reacting propylene, molecular oxygen, and ammonia in the presence of the ammoxidation catalyst, thereby obtaining acrylonitrile.

[7]

The method for producing acrylonitrile according to [6], wherein the precursor slurry has a viscosity of 1 to 100 cp.

[8]

The method for producing acrylonitrile according to [6] or [7], wherein the ammoxidation catalyst has a composition represented by the following formula (1):

$$Mo_{12}Bi_aFe_bX_cY_dZ_eO_f \quad (1);$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; provided that a proportion of cobalt is 20 atomic % or more and/or a proportion of magnesium is 20 atomic % or less in the element X; a, b, c, d, and e satisfy $0.1 \le a \le 2.0$, $0.1 \le b \le 3.0$, $0.1 \le c \le 10.0$, $0.1 \le d \le 3.0$ and $0.01 \le e \le 2.0$, respectively; and f represents a number of oxygen atoms needed to satisfy atomic valence requirements of other elements present therein.

[9]

The method for producing acrylonitrile according to any of [6] to [8], wherein a content of the carboxylic acid compound in the precursor slurry is 0.01 to 0.10 mol equivalents based on a sum of metal elements constituting the ammoxidation catalyst.

[10]

An ammoxidation catalyst for producing acrylonitrile by reacting propylene, molecular oxygen, and ammonia, comprising molybdenum, bismuth, and iron,
wherein the ammoxidation catalyst satisfies both the following requirements (1) and (2):
Requirement (1): a yield of acrylonitrile through ammoxidation reaction of propylene, which is calculated by the following measurement method A, is 84.1% or more; and
Requirement (2): an attrition loss of the ammoxidation catalyst, which is calculated by the following measurement method B, is 0.9% or less;

[Measurement Method A]

a glass pipe having an inner diameter of 25 mm, the glass pipe having 16 10-mesh wire nets built-in at an interval of 1 cm, is used as a reactor, 50 cc of the ammoxidation catalyst is packed in the reactor, a reaction temperature is set to 430° C. and a reaction pressure is set to 0.17 MPa, a mixed gas of propylene, ammonia, oxygen, and helium, the mixed gas comprising 9% by volume of propylene, is passed through the reactor, and a yield of acrylonitrile produced through ammoxidation reaction is calculated by the following expression;

$$\text{Sulfuric acid unit requirment (kg/T-AN)} = \frac{\text{Weight of sulfuric acid needed to neutralize unreacted ammonia (kg)}}{\text{Weight of acrylonitrile produced (T)}}$$

$$\text{Contact time (sec.)} = \frac{\text{Amount of catalyst }(cc)}{\text{Flow rate of mixed gas }(cc\text{-}NTP/\text{sec.})} \times \frac{273}{273 + \text{reaction temperature (° C.)}} \times \frac{\text{Reaction pressure }(MPa)}{0.10}$$

$$\text{Converstion rate of propylene (\%)} = \frac{\text{Propylene consumed (mol)}}{\text{Propylene supplied (mol)}} \times 100$$

$$\text{Acrylonitrile yield (\%)} = \frac{\text{Acrylonitrile produced (mol)}}{\text{Propylene supplied (mol)}} \times 100$$

wherein a volume ratio of ammonia to propylene is set such that the sulfuric acid unit requirement defined by the expression is 20±2 kg/T-AN; a volume ratio of oxygen to propylene is set such that an oxygen concentration in a gas at an outlet of the reactor is 0.2±0.02% by volume; and, by changing the flow rate of the mixed gas, the contact time defined by the above expression is changed to thereby set the conversion rate of propylene defined by the expression to 99.3±0.2%;

[Measurement Method B]

An attrition strength of the ammoxidation catalyst is measured in accordance with a method described in "Test Method for Synthetic Fluid Cracking Catalyst," American Cyanamid Co. Ltd. 6/31-4m-1/57, to calculate the attrition loss defined as follows:

$$\text{Attrition loss (\%)} = R/(S-Q) \times 100$$

wherein Q represents a mass (g) of the catalyst scattering to an outside of a measurement system due to attrition during a period from 0 to 5 hours, R represents a mass (g) of the catalyst scattering to the outside of the measurement system due to attrition during a period from 5 to 20 hours; and S represents a mass (g) of the catalyst supplied for the test.

[11]

The ammoxidation catalyst according to [10], having a composition represented by the following formula (1):

$$Mo_{12}Bi_aFe_bX_cY_dZ_eO_f \quad (1);$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; provided that a proportion of cobalt is 20 atomic % or more and/or a proportion of magnesium is 20 atomic % or less in the element X; a, b, c, d, and e satisfy $0.1 \le a \le 2.0$, $0.1 \le b \le 3.0$, $0.1 \le c \le 10.0$, $0.1 \le d \le 3.0$ and $0.01 \le e \le 2.0$, respectively; and f represents a number of oxygen atoms needed to satisfy atomic valence requirements of other elements present therein.

[12]

A method for producing acrylonitrile by reacting propylene, molecular oxygen, and ammonia, wherein the ammoxidation catalyst according to [10] or [11] is used.

Advantageous Effects of Invention

According to the present invention, a method for producing an ammoxidation catalyst exhibiting a high acrylonitrile yield and having a favorable attrition strength to endure long-term use as a fluidized bed catalyst, and a method for producing acrylonitrile can be provided.

DESCRIPTION OF EMBODIMENTS

Hereinafter, an embodiment for carrying out the present invention (hereinafter, simply referred to as "present embodiment") will be described, but the present invention is not limited to the following embodiment and can be modified variously within the scope thereof.

[Method for Producing Ammoxidation Catalyst]

A method for producing an ammoxidation catalyst according to the present embodiment comprises: a step (i) of preparing a starting material slurry comprising molybdenum, bismuth, iron, and a carboxylic acid compound; a step (ii) of stirring the starting material slurry in a temperature range of 30 to 50° C. for 20 minutes to 8 hours, thereby preparing a precursor slurry; a step of spray-drying the precursor slurry, thereby obtaining a dried particle; and a step of calcining the dried particle.

By allowing the method for producing an ammoxidation catalyst according to the present embodiment to have the above-described constitution, an ammoxidation catalyst exhibiting a high acrylonitrile selectivity and having favorable attrition strength to endure long-term use as a fluidized bed catalyst can be obtained. The present inventors consider this as follows. The active site in the ammoxidation reaction is present in a bismuth-containing molybdate, but the high acrylonitrile selectivity cannot be obtained with the bismuth-containing molybdate alone. It is considered that complexation of the bismuth-containing molybdate with an iron-containing molybdate and a molybdate that contains another metal improves the acrylonitrile selectivity. That is, it is considered that dispersing each metal component as a single component without causing aggregation thereof at a stage of the precursor slurry to thereby create a state, in which the bismuth-containing molybdate easily undergoes complexation with the molybdate that contains another metal, contributes to improvements in the acrylonitrile selectivity. In addition, it is considered that by preventing the aggregation of metals and carrier particles in the precursor slurry, the attrition strength of the catalyst is improved. However, the mechanism of action is not limited to those described above.

(Composition)

The ammoxidation catalyst in the present embodiment comprises molybdenum, bismuth, and iron as essential components. Molybdenum has a role as a site of adsorbing propylene and a site of activating ammonia. In addition, bismuth has a role of activating propylene and abstracting α hydrogen to produce a π allyl species. Further, iron has a role of supplying oxygen existing in a gas phase to a catalytically active site through trivalent/divalent redox.

Besides, an optional component which may be contained in the ammoxidation catalyst in the present embodiment is not particularly limited, and examples thereof include at least one element X selected from the group consisting of nickel, cobalt, magnesium, calcium, zinc, strontium, and barium, at least one element Y selected from the group consisting of cerium, chromium, lanthanum, neodymium, yttrium, praseodymium, aluminum, gallium, and indium, and at least one element Z selected from the group consisting of potassium, rubidium, and cesium. The element X forms a molybdate having a moderate amount of lattice defects and has a role of making the transfer of oxygen within a bulk smooth. In addition, the proportion of cobalt and of magnesium in the element X give a great influence on the attrition strength of the catalyst. The present inventors have found that when the proportion of cobalt of the element X becomes large, and/or the proportion of magnesium contained in the element X becomes small, there is a tendency that the acrylonitrile selectivity becomes high, which is preferable, but the viscosity of the precursor slurry at less than 30° C. in the step (ii) becomes high and the attrition strength of a resultant catalyst becomes low. Specifically, when cobalt accounts for 20 atomic % or more and/or magnesium accounts for 20 atomic % or less of the element X, there is a tendency that the viscosity of the precursor slurry at less than 30° C. in the step (ii) becomes high and the attrition strength of a resultant catalyst becomes low. However, in the production method according to the present embodiment, by stirring the starting material slurry at a temperature of 30° C. or more in the step (ii) so that the viscosity of the precursor slurry will not become high, the attrition strength of a resultant catalyst can be made favorable even when cobalt accounts for 20 atomic % or more and/or magnesium accounts for 20 atomic % or less of the element X. The element Y as well as iron has a redox function in the catalyst. Further, the element Z has a role of suppressing decomposition reaction of the main product and of the starting materials by blocking acid centers existing on the surface of the catalyst.

That is, the ammoxidation catalyst obtained by the method for producing an ammoxidation catalyst according to the present embodiment preferably has a composition represented by the following formula (1). By allowing the ammoxidation catalyst to have such a composition, there is a tendency that the acrylonitrile selectivity is further improved.

$$Mo_{12}Bi_aFe_bX_cY_dZ_eO_f \quad (1);$$

In the formula (1),

X represents at least one element selected from the group consisting of nickel, cobalt, magnesium, calcium, zinc, strontium, and barium, Y represents at least one element selected from the group consisting of cerium, chromium, lanthanum, neodymium, yttrium, praseodymium, samarium, aluminum, gallium, and indium, and Z represents at least one element selected from the group consisting of potassium, rubidium, and cesium;

a represents an atomic ratio of bismuth to 12 atoms of molybdenum, and satisfies $0.1 \leq a \leq 2.0$, preferably $0.15 \leq a \leq 1.0$, and more preferably $0.2 \leq a \leq 0.7$;

b represents an atomic ratio of iron to 12 atoms of molybdenum, and satisfies $0.1 \leq b \leq 3.0$, preferably $0.5 \leq b \leq 2.5$, and more preferably $1.0 \leq b \leq 2.0$;

c represents an atomic ratio of the X to 12 atoms of molybdenum, and satisfies $0.1 \leq c \leq 10.0$, preferably $3.0 \leq c \leq 9.0$, and more preferably $5.0 \leq c \leq 8.5$;

d represents an atomic ratio of the Y to 12 atoms of molybdenum, and satisfies $0.1 \leq c \leq 13.0$, preferably $0.2 \leq c \leq 12.0$, and more preferably $0.3 \leq c \leq 11.5$;

e represents an atomic ratio of the Z to 12 atoms of molybdenum, and satisfies $0.01 \leq e \leq 2.0$, preferably $0.05 \leq e \leq 1.0$; and f represents an atomic ratio of oxygen to 12 atoms of molybdenum and a number of oxygen atoms needed to satisfy atomic valence requirements of the other existing elements.

In a case where acrylonitrile is industrially produced, a fluidized bed reaction in which a catalyst is fluidized by a reaction gas is generally selected. Therefore, the ammoxidation catalyst preferably has a predetermined or higher strength. From such a viewpoint, the ammoxidation catalyst may be carried by a carrier. The carrier for the ammoxidation catalyst is not particularly limited, and examples thereof include oxides such as silica, alumina, titania, and zirconia. Among these, silica, with which lowering of the acrylonitrile selectivity is small, and the attrition resistance and the particle strength of the catalyst can be greatly improved, is suitable as a carrier.

The content of the carrier is preferably 30 to 70% by mass, more preferably 35 to 65% by mass, based on the total mass of the ammoxidation catalyst and the carrier. By allowing the content of the carrier to be 30% by mass or more, there is a tendency that the attrition resistance and the particle strength of the catalyst is further improved. By allowing the content of the carrier to be 70% by mass or less, there is a tendency that the acrylonitrile selectivity is further improved.

The starting material for silica to be used as a carrier is not particularly limited, but silica sol is preferable. The primary particle diameter of silica contained in silica sol is not particularly limited, and different types of silica each having a different primary particle diameter may be mixed and used.

[Method for Producing Ammoxidation Catalyst]
[Step (i)]

The step (i) is a step of preparing a starting material slurry comprising molybdenum, bismuth, iron, and a carboxylic acid compound. In this case, if necessary, silica and water may further be mixed. In the step (i), the order of mixing respective components is not particularly limited, and, for example, the starting material slurry can be obtained by preparing a solution containing molybdenum, and thereafter mixing the other metal components and a carboxylic acid compound with this solution.

The starting material for each component to be used for preparing the starting material slurry is preferably a salt that is soluble to water or nitric acid. The starting material for each element of molybdenum, bismuth, and iron is not particularly limited, and examples thereof include ammonium salts, nitrates, hydrochlorides, sulfates, organic acid salts, and inorganic salts which are soluble to water or nitric acid. Particularly, ammonium salts are preferable as the starting material for molybdenum. In addition, as the starting materials for bismuth and iron, the nitrates of the respective elements are preferable. Nitrates are also preferable in that they are easy to handle, and besides, they do not produce residue of chlorine that is produced in a case where hydrochloric acid is used, or residue of sulfur that is produced in a case where sulfuric acid is used. Examples of the starting material for each component include, but not limited to, ammonium paramolybdate, bismuth nitrate, and ferric nitrate.

As the starting material for silica, silica sol is preferable. The preferable concentration of silica sol in a state of a starting material in which other components are not mixed is 10 to 50% by mass.

The starting material slurry comprises a carboxylic acid compound. The carboxylic acid compound is a representative coordinating organic compound, and it is considered that the carboxylic acid compound facilitates enhancement of dispersibility of metal components by bonding to the metal components. The carboxylic acid compound is not particularly limited, and examples thereof include oxalic acid, tartaric acid, succinic acid, malic acid, and citric acid. Among these, oxalic acid and tartaric acid are preferable, more preferably oxalic acid. In addition, the starting material for silica and the starting material for oxalic acid are preferably mixed in advance.

The content of the carboxylic acid compound is 0.01 to 0.10 mol equivalents in the precursor slurry, which will be described later, based on the sum of the metal elements constituting the ammoxidation catalyst. The content of the carboxylic acid compound is more preferably 0.02 to 0.09 mol equivalents, still more preferably 0.02 to 0.07 mol equivalents. By allowing the content of the carboxylic acid compound to be 0.01 mol equivalents or more, there is a tendency that the acrylonitrile yield of a resultant catalyst is further improved. In addition, by allowing the content of the carboxylic acid compound to be 0.10 mol equivalents or less, there is a tendency that heat generation due to decomposition or diffusion of the carboxylic acid compound, or cracking of the catalyst particle is suppressed at a stage of producing the catalyst and the strength of a resultant catalyst is further improved. The content of the carboxylic acid compound can be adjusted in the above-described ranges according to the ratio of the starting materials added.

[Step (ii)]

The step (ii) is a step of stirring the starting material slurry at a predetermined temperature for a predetermined time, thereby preparing a precursor slurry.

The temperature during stirring is 30 to 50° C., preferably 35 to 45° C. When the temperature during stirring is 30 to 50° C., the enhancement of dispersibility of the metal components and carrier components that can be contained is facilitated, and a catalyst having favorable acrylonitrile yield and attrition strength is obtained. In a case where the temperature during stirring is lower than 30° C., the surface state of a catalyst may become rough to bring about lowering of the attrition strength in some cases. In a case where the temperature during stirring is higher than 50° C., a starting material component such as sulfuric acid may volatilize to increase the pH of the slurry, and the metal components may aggregate to bring about lowering of the acrylonitrile yield in some cases.

The stirring time is 20 minutes to 8.0 hours, preferably 2.0 to 5.0 hours. When the stirring time is 8.0 hours or less, the reaggregation of the metal components whose dispersibility has been enhanced is suppressed, and a catalyst having favorable acrylonitrile yield and attrition strength is obtained. In a case where the stirring time is more than 8.0 hours, the aggregation of the metal components may become remarkable to bring about lowering of the acrylonitrile yield in some cases. In a case where the stirring time is less than 20 minutes, mixing of the metal components may be insufficient and a lot of single oxide may be formed in calcination to bring about lowering of the acrylonitrile yield in some cases.

The viscosity of the precursor slurry is preferably 1 to 100 cp, more preferably 20 to 90 cp, and still more preferably 30 to 90 cp. When the viscosity of the precursor slurry is 1 cp or more, there is a tendency that entrainment of air bubbles during stirring is further suppressed and a catalyst having a further favorable attrition strength is obtained. When the viscosity of the precursor slurry is 100 cp or less, the aggregation of the metal components is further suppressed, and a catalyst having further favorable acrylonitrile yield and attrition strength is obtained. The viscosity can be measured by the method described in Examples, which will be described later. In addition, the viscosity can be adjusted in the above-described ranges according to, for example, the temperature of the starting material slurry, the stirring time, and the stirring speed. Specifically, for example, when the temperature of the starting material slurry is made high, there is a tendency that the viscosity becomes low, when the temperature of the starting material slurry is made low, there is a tendency that the viscosity becomes high, when the stirring time is made long, there is a tendency that the viscosity becomes low, and when the stirring speed is made large, there is a tendency that the viscosity becomes low. From such viewpoints, the temperature of the starting material slurry is preferably set to 35° C. or more.

[Drying Step]

The drying step is a step of spray-drying the precursor slurry obtained in the step (ii), thereby obtaining a dried particle. By spray-drying the precursor slurry, a spherical, fine particle suitable for fluidized bed reaction can be obtained. As a spray-drying apparatus, a general apparatus such as a rotary disk type or nozzle type apparatus can be used. By adjusting spray-drying conditions, the particle diameter of the catalyst can be adjusted. In a case where the catalyst is used as a fluidized bed catalyst, the particle diameter of the catalyst is preferably 25 to 180 µm. An example of the condition for obtaining a catalyst particle having a preferable particle diameter includes spray-drying performed using a centrifugal nebulization apparatus provided with a dish type rotor installed at the center of the upper portion of a drier, and holding the temperature of air at the inlet of the drier at 180 to 250° C. and the temperature at the outlet at 100 to 150° C.

[Calcination Step]

The calcination step is a step of calcining the dried particle obtained in the drying step. In a case where the dried particle contains nitric acid, a denitration treatment is preferably performed before the calcination. The denitration treatment is preferably performed at 150 to 450° C. for 1.5 to 3 hours. The calcination can be performed in an air atmosphere. The calcination temperature is preferably 550 to 650° C. By allowing the calcination temperature to be 550° C. or more, there is a tendency that crystal growth progresses sufficiently and the acrylonitrile selectivity of a resultant catalyst is further improved. In addition, by allowing the calcination temperature to be 650° C. or less, there is a tendency that the specific surface area of a catalyst that can be obtained is increased and the reaction activity of propylene is further improved.

[Ammoxidation Catalyst]

The ammoxidation catalyst according to the present embodiment is an ammoxidation catalyst for producing acrylonitrile by reacting propylene, molecular oxygen, and ammonia, the ammoxidation catalyst comprising molybdenum, bismuth, and iron, and satisfying both the following requirements (1) and (2).

Requirement (1): a yield of acrylonitrile through ammoxidation reaction of propylene, which is calculated by the following measurement method A, is 84.1% or more.

Requirement (2): an attrition loss of the ammoxidation catalyst, which is calculated by the following measurement method B, is 0.9% or less;

[Measurement Method A]

A glass pipe having an inner diameter of 25 mm, the glass pipe having 16 10-mesh wire nets built-in at an interval of 1 cm, is used as a reactor, 50 cc of the ammoxidation catalyst is packed in the reactor, a reaction temperature is set to 430° C. and a reaction pressure is set to 0.17 MPa, a mixed gas of propylene, ammonia, oxygen, and helium, the mixed gas comprising 9% by volume of propylene, is passed through the reactor, and a yield of acrylonitrile produced through ammoxidation reaction is calculated by the following expression.

$$\text{Sulfuric acid unit requirment (kg/T-AN)} = \frac{\text{Weight of sulfuric acid needed to neutralize unreacted ammonia (kg)}}{\text{Weight of acrylonitrile produced }(T)}$$

$$\text{Contact time (sec.)} = \frac{\text{Amount of catalyst }(cc)}{\text{Flow rate of mixed gas }(cc\text{-}NTP/\text{sec.})} \times \frac{273}{273 + \text{reaction temperature (° C.)}} \times \frac{\text{Reaction pressure }(MPa)}{0.10}$$

$$\text{Converstion rate of propylene (\%)} = \frac{\text{Propylene consumed (mol)}}{\text{Propylene supplied (mol)}} \times 100$$

$$\text{Acrylonitrile yield (\%)} = \frac{\text{Acrylonitrile produced (mol)}}{\text{Propylene supplied (mol)}} \times 100$$

wherein a volume ratio of ammonia to propylene is set such that a sulfuric acid unit requirement defined by the expression is 20±2 kg/T-AN; a volume ratio of oxygen to propylene is set such that an oxygen concentration of a gas at an outlet of a reactor is 0.2±0.02% by volume; and, by changing a flow rate of the mixed gas, the contact time defined by the above expression is changed such that the conversion rate of propylene defined by the expression to 99.3±0.2%.

[Measurement Method B]

Attrition strength of the ammoxidation catalyst is measured in accordance with a method described in "Test Method for Synthetic Fluid Cracking Catalyst" (American Cyanamid Co. Ltd. 6/31-4m-1/57) to calculate an attrition loss defined as follows.

$$\text{Attrition loss (\%)} = R/(S-Q) \times 100$$

wherein Q represents a mass (g) of the catalyst scattering to an outside of a measurement system due to attrition during the period from 0 to 5 hours; R represents a mass (g) of the catalyst scattering to the outside of the measurement system due to attrition during the period from 5 to 20 hours; and S represents a mass (g) of the catalyst supplied for the test.

It can be deemed that the ammoxidation catalyst according to the present embodiment is constituted as described above, and therefore exhibits a high acrylonitrile yield and has a favorable attrition strength to endure long-term use as a fluidized bed catalyst. The above-described acrylonitrile yield and attrition loss can be adjusted in the above-described ranges, for example, by adopting a desired condition in the above-described step (ii) of the method for producing an ammoxidation catalyst according to the present embodiment, or by other methods.

The ammoxidation catalyst according to the present embodiment preferably has a composition represented by the formula (1).

[Method for Producing Acrylonitrile]

A method for producing acrylonitrile according to the present embodiment comprises a reaction step of reacting propylene, molecular oxygen, and ammonia in the presence of the above-described ammoxidation catalyst, thereby producing acrylonitrile. The method for producing acrylonitrile according to the present embodiment can also be performed subsequently to the above-described method for producing an ammoxidation catalyst. That is, the method for producing acrylonitrile according to the present embodiment can comprise: a step (i) of preparing a starting material slurry comprising molybdenum, bismuth, iron, and a carboxylic acid compound; a step (ii) of stirring the starting material slurry in the temperature range of 30 to 50° C. for 20 minutes to 8 hours, thereby preparing a precursor slurry; a step of spray-drying the precursor slurry, thereby obtaining a dried particle; a step of calcining the dried particle, thereby obtaining an ammoxidation catalyst; and a step of reacting propylene, molecular oxygen, and ammonia in the presence of the ammoxidation catalyst, thereby obtaining acrylonitrile.

Production of acrylonitrile through ammoxidation reaction can be performed by a fixed bed reactor or a fluidized bed reactor. Among these, the fluidized bed reactor is preferable from the viewpoint of efficiently removing heat generated during reaction and enhancing the yield of acrylonitrile.

Propylene and ammonia each being a starting material in the ammoxidation reaction are not necessarily of high purity, and propylene and ammonia of industrial grade can be used. The molar ratio of propylene, ammonia, and oxygen (propylene/ammonia/oxygen) in the starting material gas is preferably 1.0/1.0 to 1.5/1.6 to 2.2.

The reaction temperature is preferably 380 to 480° C. In addition, the reaction pressure is preferably normal pressure to 0.3 MPa. The contact time between the starting material gas and the catalyst is preferably 2 to 7 seconds, more preferably 3 to 6 seconds.

EXAMPLES

Hereinafter, the present embodiment will be described in more detail giving Examples, but the present embodiment is not limited to Examples described below. It is to be noted that the catalyst composition described in Examples and Comparative examples has the same value as the composition of each element added.

Example 1

A catalyst, in which a metal oxide having a composition represented by $Mo_{12.00}Bi_{0.37}Fe_{1.53}Co_{4.11}Ni_{3.30}Ce_{0.81}Rb_{0.14}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.039 mol equivalents based on the sum of the metal elements). Subsequently, to the resultant mixture, 481.9 g of ammonium paramolybdate $[(NH_4)_6Mo_7O_{24}.4H_2O]$ dissolved in 866.3 g of water was added under stirring, and further 41.1 g of bismuth nitrate $[Bi(NO_3)_3.5H_2O]$, 140.6 g of iron nitrate $[Fe(NO_3)_3.9H_2O]$, 272.3 g of cobalt nitrate $[Co(NO_3)_2.6H_2O]$, 218.2 g of nickel nitrate $[Ni(NO_3)_2.6H_2O]$, 80.3 g of cerium nitrate $[Ce(NO_3)_3.6H_2O]$, and 4.81 g of rubidium nitrate $[RbNO_3]$ dissolved in 393.8 g of 16.6% by mass of nitric acid were added to prepare a starting material slurry. The starting material slurry was stirred at 33° C. for 3.5 hours to prepare a precursor slurry. The viscosity of the resultant precursor slurry was 62 cp. It is to be noted that the viscosity of the precursor slurry is measured with a B type viscometer ("TVB-10" manufactured by TOKI SANGYO CO., LTD.), and the same applies to Examples and Comparative Examples below. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 590° C. for 2 hours to obtain a catalyst.

Example 2

A catalyst was produced in the same manner as in Example 1 except that the starting material slurry was stirred at 40° C. for 3.5 hours. On that occasion, the viscosity of the slurry was 51 cp.

Example 3

A catalyst was produced in the same manner as in Example 1 except that the starting material slurry was stirred at 46° C. for 3.5 hours. On that occasion, the viscosity of the slurry was 45 cp.

Example 4

A catalyst was produced in the same manner as in Example 1 except that the starting material slurry was stirred at 40° C. for 1 hour. On that occasion, the viscosity of the slurry was 63 cp.

Example 5

A catalyst was produced in the same manner as in Example 1 except that the starting material slurry was stirred at 41° C. for 6 hours. On that occasion, the viscosity of the slurry was 42 cp.

Example 6

A catalyst was produced in the same manner as in Example 1 except that 22.5 g of tartaric acid dissolved in 200 g of water was added (in the precursor slurry, 0.030 mol equivalents based on the sum of the metal elements) in place of oxalic acid dihydrate to the silica sol and that the starting material slurry was stirred at 40° C. for 3.5 hours. On that occasion, the viscosity of the slurry was 46 cp.

Example 7

A catalyst, in which a metal oxide having a composition represented by $Mo_{12.00}Bi_{0.39}Fe_{1.60}Ni_{6.97}Mg_{0.77}Ce_{0.63}Rb_{0.17}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.038 mol equivalents based on the sum of the metal elements). To the resultant mixture, 485.9 g of ammonium paramolybdate $[(NH_4)_6Mo_7O_{24}.4H_2O]$ dissolved in 873.5 g of water was added under stirring, and further 43.1 g of bismuth nitrate $[Bi(NO_3)_3.5H_2O]$, 148.0 g of iron nitrate $[Fe(NO_3)_3.9H_2O]$, 464.7 g of nickel nitrate $[Ni(NO_3)_2.6H_2O]$, 45.5 g of magnesium nitrate $[Mg(NO_3)_2.6H_2O]$, 62.6 g of cerium nitrate $[Ce(NO_3)_3.6H_2O]$, and 5.89 g of rubidium nitrate $[RbNO_3]$ dissolved in 396.7 g of 16.6% by mass of nitric acid were added to prepare a starting material slurry. The starting material slurry was stirred at 32° C. for 3.5 hours to prepare a precursor slurry. The viscosity of the resultant precursor slurry was 105 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 580° C. for 2 hours to obtain a catalyst.

Example 8

A catalyst was produced in the same manner as in Example 7 except that the starting material slurry was stirred at 41° C. for 3.5 hours. On that occasion, the viscosity of the slurry was 81 cp.

Example 9

A catalyst was produced in the same manner as in Example 7 except that 22.5 g of tartaric acid dissolved in 200 g of water was added (in the precursor slurry, 0.028 mol equivalents based on the sum of the metal elements) in place of oxalic acid dihydrate to the silica sol and that the starting material slurry was stirred at 40° C. for 3.5 hours. On that occasion, the viscosity of the slurry was 74 cp.

Example 10

A catalyst, in which a metal oxide having a composition represented by $Mo_{12.00}Bi_{1.20}Fe_{0.60}Ni_{7.80}Cr_{1.20}K_{0.48}$ is carried on 60% by mass of silica, was produced according to the following procedure.

To 2000 g of silica sol containing 30% by mass of $SiO_2$, 25.0 g of oxalic acid dihydrate dissolved in 200 g of water was added (in the precursor slurry, 0.059 mol equivalents based on the sum of the metal elements). To the resultant mixture, 308.0 g of ammonium paramolybdate $[(NH_4)_6Mo_7O_{24}.4H_2O]$ dissolved in 553.7 g of water was added under stirring, and further 84.6 g of bismuth nitrate $[Bi(NO_3)_3.5H_2O]$, 35.2 g of iron nitrate $[Fe(NO_3)_3.9H_2O]$, 329.8 g of nickel nitrate $[Ni(NO_3)_2.6H_2O]$, 69.8 g of chromium nitrate $[Cr(NO_3)_3.9H_2O]$, and 7.06 g of potassium nitrate $[KNO_3]$ dissolved in 387.6 g of 16.6% by mass of nitric acid were added to prepare a starting material slurry.

The starting material slurry was stirred at 42° C. for 3.5 hours to prepare a precursor slurry. The viscosity of the resultant precursor slurry was 43 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 590° C. for 2 hours to obtain a catalyst.

Example 11

A catalyst, in which a metal oxide having a composition represented by $Mo_{12.00}Bi_{0.57}Fe_{1.01}Co_{6.83}Ni_{0.98}Mg_{0.98}Ce_{0.38}Rb_{0.12}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.038 mol equivalents based on the sum of the metal elements). To the resultant mixture, 482.0 g of ammonium paramolybdate $[(NH_4)_6Mo_7O_{24}.4H_2O]$ dissolved in 866.4 g of water was added under stirring, and further 62.7 g of bismuth nitrate $[Bi(NO_3)_3.5H_2O]$, 93.0 g of iron nitrate $[Fe(NO_3)_3.9H_2O]$, 452.3 g of cobalt nitrate $[Co(NO_3)_2.6H_2O]$, 64.5 g of nickel nitrate $[Ni(NO_3)_2.6H_2O]$, 56.9 g of magnesium nitrate $[Mg(NO_3)_2.6H_2O]$, 37.4 g of cerium nitrate $[Ce(NO_3)_3.6H_2O]$, and 3.93 g of rubidium nitrate $[RbNO_3]$ dissolved in 395.2 g of 16.6% by mass of nitric acid were added to prepare a starting material slurry.

The starting material slurry was stirred at 32° C. for 3.5 hours to prepare a precursor slurry. The viscosity of the resultant precursor slurry was 73 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 590° C. for 2 hours to obtain a catalyst.

Example 12

A catalyst was produced in the same manner as in Example 11 except that the starting material slurry was stirred at 40° C. for 3.5 hours. On that occasion, the viscosity of the slurry was 58 cp.

Example 13

A catalyst was produced in the same manner as in Example 11 except that the starting material slurry was stirred at 47° C. for 3.5 hours. On that occasion, the viscosity of the slurry was 50 cp.

Example 14

A catalyst was produced in the same manner as in Example 11 except that the starting material slurry was stirred at 41° C. for 1 hour. On that occasion, the viscosity of the slurry was 74 cp.

Example 15

A catalyst was produced in the same manner as in Example 11 except that the starting material slurry was stirred at 40° C. for 6 hours. On that occasion, the viscosity of the slurry was 49 cp.

Example 16

A catalyst was produced in the same manner as in Example 7 except that 22.5 g of tartaric acid dissolved in 200 g of water was added (in the precursor slurry, 0.029 mol equivalents based on the sum of the metal elements) in place of oxalic acid dihydrate to the silica sol and that the starting material slurry was stirred at 40° C. for 3.5 hours. On that occasion, the viscosity of the slurry was 40 cp.

Example 17

A catalyst, in which a metal oxide having a composition represented by $Mo_{12.00}Bi_{0.57}Fe_{1.01}Co_{2.24}Ni_{6.54}Ce_{0.38}Rb_{0.12}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.039 mol equivalents based on the sum of the metal elements). To the resultant mixture, 479.5 g of ammonium paramolybdate [$(NH_4)_6Mo_7O_{24}.4H_2O$] dissolved in 855.9 g of water was added under stirring, and further 61.9 g of bismuth nitrate [$Bi(NO_3)_3.5H_2O$], 91.9 g of iron nitrate [$Fe(NO_3)_3.9H_2O$], 146.8 g of cobalt nitrate [$Co(NO_3)_2.6H_2O$], 427.2 g of nickel nitrate [$Ni(NO_3)_2.6H_2O$], 36.9 g of cerium nitrate [$Ce(NO_3)_3.6H_2O$], and 3.88 g of rubidium nitrate [$RbNO_3$] dissolved in 393.2 g of 16.6% by mass of nitric acid were added to prepare a starting material slurry.

The starting material slurry was stirred at 38° C. for 3.5 hours to prepare a precursor slurry. The viscosity of the resultant precursor slurry was 85 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 600° C. for 2 hours to obtain a catalyst.

Example 18

A catalyst, in which a metal oxide having a composition represented by $Mo_{12.00}Bi_{0.82}Fe_{1.45}Co_{8.14}Ce_{0.55}Rb_{0.13}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.039 mol equivalents based on the sum of the metal elements). To the resultant mixture, 462.7 g of ammonium paramolybdate [$(NH_4)_6Mo_7O_{24}.4H_2O$] dissolved in 855.9 g of water was added under stirring, and further 88.5 g of bismuth nitrate [$Bi(NO_3)_3.5H_2O$], 128.2 g of iron nitrate [$Fe(NO_3)_3.9H_2O$], 517.3 g of cobalt nitrate [$Co(NO_3)_2.6H_2O$], 52.4 g of cerium nitrate [$Ce(NO_3)_3.6H_2O$], and 4.06 g of rubidium nitrate [$RbNO_3$] dissolved in 391.1 g of 16.6% by mass of nitric acid were added to prepare a starting material slurry.

The starting material slurry was stirred at 39° C. for 3.5 hours to prepare a precursor slurry. The viscosity of the resultant precursor slurry was 80 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 585° C. for 2 hours to obtain a catalyst.

Example 19

A catalyst, in which a metal oxide having a composition represented by $Mo_{12.00}Bi_{1.05}Fe_{1.40}Co_{8.15}Ce_{0.70}Rb_{0.13}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.040 mol equivalents based on the sum of the metal elements). To the resultant mixture, 450.8 g of ammonium paramolybdate [$(NH_4)_6Mo_7O_{24}.4H_2O$] dissolved in 810.3 g of water was added under stirring, and further 108.1 g of bismuth nitrate [$Bi(NO_3)_3.5H_2O$], 120.1 g of iron nitrate [$Fe(NO_3)_3.9H_2O$], 504.7 g of cobalt nitrate [$Co(NO_3)_2.6H_2O$], 64.5 g of cerium nitrate [$Ce(NO_3)_3.6H_2O$], and 3.96 g of rubidium nitrate [$RbNO_3$] dissolved in 388.6 g of 16.6% by mass of nitric acid were added to prepare a starting material slurry.

The starting material slurry was stirred at 40° C. for 3.5 hours to prepare a precursor slurry. The viscosity of the resultant precursor slurry was 74 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 585° C. for 2 hours to obtain a catalyst.

Example 20

A catalyst, in which a metal oxide having a composition represented by $Mo_{12.00}Bi_{0.84}Fe_{2.06}Co_{6.67}Ce_{0.56}Rb_{0.12}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.040 mol equivalents based on the sum of the metal elements). To the resultant mixture, 472.5 g of ammonium paramolybdate [$(NH_4)_6Mo_7O_{24}.4H_2O$] dissolved in 849.4 g of water was added under stirring, and further 90.7 g of bismuth nitrate [$Bi(NO_3)_3.5H_2O$], 185.4 g of iron nitrate [$Fe(NO_3)_3.9H_2O$], 432.8 g of cobalt nitrate [$Co(NO_3)_2.6H_2O$], 54.4 g of cerium nitrate [$Ce(NO_3)_3.6H_2O$], and 3.96 g of rubidium nitrate [$RbNO_3$] dissolved in 391.6 g of 16.6% by mass of nitric acid were added to prepare a starting material slurry.

The starting material slurry was stirred at 40° C. for 3.5 hours to prepare a precursor slurry. The viscosity of the resultant precursor slurry was 106 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 580° C. for 2 hours to obtain a catalyst.

Example 21

A catalyst, in which a metal oxide having a composition represented by $Mo_{12.00}Bi_{0.27}Fe_{0.95}Co_{9.64}Ce_{0.18}Rb_{0.13}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.038 mol equivalents based on the sum of the metal elements). To the resultant mixture, 483.6 g of ammonium paramolybdate $[(NH_4)_6Mo_7O_{24}.4H_2O]$ dissolved in 869.3 g of water was added under stirring, and further 29.4 g of bismuth nitrate $[Bi(NO_3)_3.5H_2O]$, 88.0 g of iron nitrate $[Fe(NO_3)_3.9H_2O]$, 640.5 g of cobalt nitrate $[Co(NO_3)_2.6H_2O]$, 17.5 g of cerium nitrate $[Ce(NO_3)_3.6H_2O]$, and 4.31 g of rubidium nitrate $[RbNO_3]$ dissolved in 396.7 g of 16.6% by mass of nitric acid were added to prepare a starting material slurry.

The starting material slurry was stirred at 41° C. for 3.5 hours to prepare a precursor slurry. The viscosity of the resultant precursor slurry was 90 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 590° C. for 2 hours to obtain a catalyst.

Example 22

A catalyst, in which a metal oxide having a composition represented by $Mo_{12.00}Bi_{0.27}Fe_{0.95}Co_{8.16}Ni_{1.48}Ce_{0.18}Rb_{0.13}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.038 mol equivalents based on the sum of the metal elements). To the resultant mixture, 483.7 g of ammonium paramolybdate $[(NH_4)_6Mo_7O_{24}.4H_2O]$ dissolved in 869.4 g of water was added under stirring, and further 29.4 g of bismuth nitrate $[Bi(NO_3)_3.5H_2O]$, 88.0 g of iron nitrate $[Fe(NO_3)_3.9H_2O]$, 542.5 g of cobalt nitrate $[Co(NO_3)_2.6H_2O]$, 98.0 g of nickel nitrate $[Ni(NO_3)_2.6H_2O]$, 17.6 g of cerium nitrate $[Ce(NO_3)_3.6H_2O]$, and 4.31 g of rubidium nitrate $[RbNO_3]$ dissolved in 396.7 g of 16.6% by mass of nitric acid were added to prepare a starting material slurry.

The starting material slurry was stirred at 40° C. for 3.5 hours to prepare a precursor slurry. The viscosity of the resultant precursor slurry was 64 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 585° C. for 2 hours to obtain a catalyst.

Example 23

A catalyst, in which a metal oxide having a composition represented by $Mo_{12.00}Bi_{0.27}Fe_{0.95}Co_{7.67}Ni_{1.97}Ce_{0.18}Rb_{0.13}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.038 mol equivalents based on the sum of the metal elements). To the resultant mixture, 483.7 g of ammonium paramolybdate $[(NH_4)_6Mo_7O_{24}.4H_2O]$ dissolved in 869.4 g of water was added under stirring, and further 29.4 g of bismuth nitrate $[Bi(NO_3)_3.5H_2O]$, 88.0 g of iron nitrate $[Fe(NO_3)_3.9H_2O]$, 509.9 g of cobalt nitrate $[Co(NO_3)_2.6H_2O]$, 130.6 g of nickel nitrate $[Ni(NO_3)_2.6H_2O]$, 17.6 g of cerium nitrate $[Ce(NO_3)_3.6H_2O]$, and 4.31 g of rubidium nitrate $[RbNO_3]$ dissolved in 396.8 g of 16.6% by mass of nitric acid were added to prepare a starting material slurry.

The starting material slurry was stirred at 39° C. for 3.5 hours to prepare a precursor slurry. The viscosity of the resultant precursor slurry was 74 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 590° C. for 2 hours to obtain a catalyst.

Example 24

A catalyst, in which a metal oxide having a composition represented by $Mo_{12.00}Bi_{0.27}Fe_{0.95}Co_{6.69}Ni_{2.95}Ce_{0.18}Rb_{0.13}$ is carried on 40% by mass of silica, was produced according to the following procedure.

To 1333 g of silica sol containing 30% by mass of $SiO_2$, 25.0 g of oxalic acid dihydrate dissolved in 200 g of water was added (in the precursor slurry, 0.038 mol equivalents based on the sum of the metal elements). To the resultant mixture, 483.7 g of ammonium paramolybdate $[(NH_4)_6Mo_7O_{24}.4H_2O]$ dissolved in 869.5 g of water was added under stirring, and further 29.4 g of bismuth nitrate $[Bi(NO_3)_3.5H_2O]$, 88.0 g of iron nitrate $[Fe(NO_3)_3.9H_2O]$, 444.5 g of cobalt nitrate $[Co(NO_3)_2.6H_2O]$, 195.9 g of nickel nitrate $[Ni(NO_3)_2.6H_2O]$, 17.6 g of cerium nitrate $[Ce(NO_3)_3.6H_2O]$, and 4.31 g of rubidium nitrate $[RbNO_3]$ dissolved in 396.8 g of 16.6% by mass of nitric acid were added to prepare a starting material slurry.

The starting material slurry was stirred at 40° C. for 3.5 hours to prepare a precursor slurry. The viscosity of the resultant precursor slurry was 71 cp. Subsequently, the precursor slurry was dried using a rotary disk type spray drier. On that occasion, the temperature of air at the inlet of the drier was set to 230° C., and the temperature of air at the outlet was set to 110° C. In addition, the number of revolutions of the disk was set to 12500 revolutions/min. The resultant dried body was held at 200° C. for 5 minutes, the temperature was then raised from 200° C. to 450° C. at 2.5° C./min., and the dried body was then held at 450° C. for 20 minutes to perform denitration. The resultant denitrated powder was calcined at 595° C. for 2 hours to obtain a catalyst.

Comparative Example 1

A catalyst was produced in the same manner as in Example 1 except that the starting material slurry was stirred at 20° C. for 3.5 hours. On that occasion, the viscosity of the slurry was 129 cp.

Comparative Example 2

A catalyst was produced in the same manner as in Example 1 except that the starting material slurry was stirred at 40° C. for 24 hours. On that occasion, the viscosity of the slurry was 31 cp.

Comparative Example 3

A catalyst was produced in the same manner as in Example 1 except that the starting material slurry was stirred at 40° C. for 0.1 hours. On that occasion, the viscosity of the slurry was 71 cp.

Comparative Example 4

A catalyst was produced in the same manner as in Example 1 except that the starting material slurry was stirred at 41° C. for 3.5 hours without adding oxalic acid dihydrate. On that occasion, the viscosity of the slurry was 70 cp.

Comparative Example 5

A catalyst was produced in the same manner as in Example 1 except that the starting material slurry was stirred at 20° C. for 3.5 hours without adding oxalic acid dihydrate. On that occasion, the viscosity of the slurry was 135 cp.

Comparative Example 6

A catalyst was produced in the same manner as in Example 1 except that the starting material slurry was stirred at 40° C. for 10 hours. On that occasion, the viscosity of the slurry was 40 cp.

Comparative Example 7

A catalyst was produced in the same manner as in Example 7 except that the starting material slurry was stirred at 22° C. for 3.5 hours. On that occasion, the viscosity of the slurry was 136 cp.

Comparative Example 8

A catalyst was produced in the same manner as in Example 7 except that the starting material slurry was stirred at 55° C. for 3.5 hours. On that occasion, the viscosity of the slurry was 65 cp.

Comparative Example 9

A catalyst was produced in the same manner as in Example 9 except that the starting material slurry was stirred at 20° C. for 3.5 hours. On that occasion, the viscosity of the slurry was 107 cp.

Comparative Example 10

A catalyst was produced in the same manner as in Example 10 except that the starting material slurry was stirred at 23° C. for 3.5 hours. On that occasion, the viscosity of the slurry was 103 cp.

Comparative Example 11

A catalyst was produced in the same manner as in Example 11 except that the starting material slurry was stirred at 19° C. for 3.5 hours. On that occasion, the viscosity of the slurry was 140 cp.

Comparative Example 12

A catalyst was produced in the same manner as in Example 11 except that the starting material slurry was stirred at 40° C. for 24 hours. On that occasion, the viscosity of the slurry was 33 cp.

Comparative Example 13

A catalyst was produced in the same manner as in Example 11 except that the starting material slurry was stirred at 40° C. for 0.1 hours. On that occasion, the viscosity of the slurry was 85 cp.

Comparative Example 14

A catalyst was produced in the same manner as in Example 11 except that the starting material slurry was stirred at 41° C. for 3.5 hours without adding oxalic acid dihydrate. On that occasion, the viscosity of the slurry was 83 cp.

Comparative Example 15

A catalyst was produced in the same manner as in Example 11 except that the starting material slurry was stirred at 21° C. for 3.5 hours without adding oxalic acid dihydrate. On that occasion, the viscosity of the slurry was 142 cp.

Comparative Example 16

A catalyst was produced in the same manner as in Example 11 except that the starting material slurry was stirred at 40° C. for 10 hours. On that occasion, the viscosity of the slurry was 42 cp.

Comparative Example 17

A catalyst was produced in the same manner as in Example 17 except that the starting material slurry was stirred at 20° C. for 3.5 hours. On that occasion, the viscosity of the slurry was 111 cp.

Comparative Example 18

A catalyst was produced in the same manner as in Example 18 except that the starting material slurry was stirred at 19° C. for 3.5 hours. On that occasion, the viscosity of the slurry was 96 cp.

21

Comparative Example 19

A catalyst was produced in the same manner as in Example 19 except that the starting material slurry was stirred at 21° C. for 3.5 hours. On that occasion, the viscosity of the slurry was 86 cp.

Comparative Example 20

A catalyst was produced in the same manner as in Example 20 except that the starting material slurry was stirred at 20° C. for 3.5 hours. On that occasion, the viscosity of the slurry was 125 cp.

Comparative Example 21

A catalyst was produced in the same manner as in Example 21 except that the starting material slurry was stirred at 20° C. for 3.5 hours. On that occasion, the viscosity of the slurry was 106 cp.

Comparative Example 22

A catalyst was produced in the same manner as in Example 22 except that the starting material slurry was stirred at 22° C. for 3.5 hours. On that occasion, the viscosity of the slurry was 84 cp.

Comparative Example 23

A catalyst was produced in the same manner as in Example 23 except that the starting material slurry was stirred at 18° C. for 3.5 hours. On that occasion, the viscosity of the slurry was 91 cp.

Comparative Example 24

A catalyst was produced in the same manner as in Example 24 except that the starting material slurry was stirred at 20° C. for 3.5 hours. On that occasion, the viscosity of the slurry was 82 cp.

Comparative Example 25

A catalyst was produced in the same manner as in Example 24 except that the starting material slurry was stirred at 39° C. for 24 hours. On that occasion, the viscosity of the slurry was 52 cp.

The production conditions for the catalysts obtained in Examples 1 to 24 and Comparative Examples 1 to 25 and the compositions of the catalysts are shown in Table 1.

[Ammoxidation Reaction Conditions and Results]

A Pyrex (R) glass pipe having an inner diameter of 25 mm, the glass pipe having 16 10-mesh wire nets built-in at an interval of 1 cm, was used as a reaction pipe to be used for ammoxidation reaction of propylene. The amount of the catalyst was set to 50 cc, the reaction temperature was set to 430° C., the reaction pressure was set to 0.17 MPa, and a mixed gas (propylene, ammonia, oxygen, helium) comprising 9% by volume of propylene was passed through the glass pipe. The molar ratio of ammonia/propylene and the molar ratio of oxygen/propylene in each of Examples and Comparative Examples are set to the values shown in Table 2. The volume ratio of ammonia to propylene was set such that a sulfuric acid unit requirement defined by the following expression was 20±2 kg/T-AN. The volume ratio of oxygen to propylene was set such that an oxygen concentration of a gas at the outlet of the reactor was 0.2±0.02% by volume. In addition, the contact time defined by the following expression was changed by changing the flow rate of the mixed gas. The contact time was set such that the conversion rate of propylene, the conversion rate defined by the following expression, was thereby 99.3±0.2%. The yield of acrylonitrile produced through the reaction was determined as a value defined by the following expression.

$$\text{Sulfuric acid unit requirment (kg/}T\text{-}AN\text{)} = \frac{\text{Weight of sulfuric acid needed to neutralize unreacted ammonia (kg)}}{\text{Weight of acrylonitrile produced }(T)}$$

$$\text{Contact time (sec.)} = \frac{\text{Amount of catalyst }(cc)}{\text{Flow rate of mixed gas }(cc\text{-}NTP/\text{sec.})} \times \frac{273}{273 + \text{reaction temperature (° C.)}} \times \frac{\text{Reaction pressure }(MPa)}{0.10}$$

$$\text{Converstion rate of propylene (\%)} = \frac{\text{Propylene consumed (mol)}}{\text{Propylene supplied (mol)}} \times 100$$

$$\text{Acrylonitrile yield (\%)} = \frac{\text{Acrylonitrile produced (mol)}}{\text{Propylene supplied (mol)}} \times 100$$

[Measurement of Attrition Strength]

As the attrition loss, the attrition strength for the catalysts was measured in accordance with the method described in "Test Method for Synthetic Fluid Cracking Catalyst" (American Cyanamid Co. Ltd. 6/31-4m-1/57) (hereinafter, referred to as "ACC method").

The attrition strength is evaluated as the attrition loss, and the attrition loss was determined as a value defined as described below.

Attrition loss (%)=$R/(S-Q) \times 100$

In the expression, Q represents a mass (g) of the catalyst scattering to an outside of a measurement system due to attrition during the period from 0 to 5 hours; R represents a mass (g) of the catalyst scattering to the outside of the measurement system due to attrition during the period from 5 to 20 hours; and S represents a mass (g) of the catalyst supplied for the test.

The reaction conditions, the reaction results, and the attrition strength for the catalysts obtained in Examples and Comparative Examples are shown in Table 2. In Table 2, the "AN yield" represents the acrylonitrile yield, and the "ATT strength" represents the attrition strength. It is to be noted that the reaction time was set to 20 hours.

TABLE 1

| | Mo | Bi | Fe | Co | Ni | Mg | X Ce | Cr | Y Rb | K | Z Carboxylic acid | Viscosity cp | Temperature ° C. | Stirring time h |
|---|---|---|---|---|---|---|---|---|---|---|---|---|---|---|
| Example 1 | 12.00 | 0.37 | 1.53 | 4.11 | 3.30 | | 0.81 | | 0.14 | | Oxalic acid | 62 | 33 | 3.5 |
| Example 2 | 12.00 | 0.37 | 1.53 | 4.11 | 3.30 | | 0.81 | | 0.14 | | Oxalic acid | 51 | 40 | 3.5 |

TABLE 1-continued

| | Mo | Bi | Fe | X Co | X Ni | X Mg | Y Ce | Y Cr | Z Rb | Z K | Carboxylic acid | Viscosity cp | Temperature °C. | Stirring time h |
|---|---|---|---|---|---|---|---|---|---|---|---|---|---|---|
| Example 3 | 12.00 | 0.37 | 1.53 | 4.11 | 3.30 | | 0.81 | 0.14 | | | Oxalic acid | 45 | 46 | 3.5 |
| Example 4 | 12.00 | 0.37 | 1.53 | 4.11 | 3.30 | | 0.81 | 0.14 | | | Oxalic acid | 63 | 40 | 1 |
| Example 5 | 12.00 | 0.37 | 1.53 | 4.11 | 3.30 | | 0.81 | 0.14 | | | Oxalic acid | 42 | 41 | 6 |
| Example 6 | 12.00 | 0.37 | 1.53 | 4.11 | 3.30 | | 0.81 | 0.14 | | | Tartaric acid | 46 | 40 | 3.5 |
| Example 7 | 12.00 | 0.39 | 1.60 | | 6.97 | 0.77 | 0.63 | 0.17 | | | Oxalic acid | 105 | 32 | 3.5 |
| Example 8 | 12.00 | 0.39 | 1.60 | | 6.97 | 0.77 | 0.63 | 0.17 | | | Oxalic acid | 81 | 41 | 3.5 |
| Example 9 | 12.00 | 0.39 | 1.60 | | 6.97 | 0.77 | 0.63 | 0.17 | | | Tartaric acid | 74 | 40 | 3.5 |
| Example 10 | 12.00 | 1.20 | 0.60 | | 7.80 | | | 1.20 | — | 0.48 | Oxalic acid | 43 | 42 | 3.5 |
| Example 11 | 12.00 | 0.57 | 1.01 | 6.83 | 0.98 | 0.98 | 0.38 | 0.12 | | | Oxalic acid | 73 | 32 | 3.5 |
| Example 12 | 12.00 | 0.57 | 1.01 | 6.83 | 0.98 | 0.98 | 0.38 | 0.12 | | | Oxalic acid | 58 | 40 | 3.5 |
| Example 13 | 12.00 | 0.57 | 1.01 | 6.83 | 0.98 | 0.98 | 0.38 | 0.12 | | | Oxalic acid | 50 | 47 | 3.5 |
| Example 14 | 12.00 | 0.57 | 1.01 | 6.83 | 0.98 | 0.98 | 0.38 | 0.12 | | | Oxalic acid | 74 | 41 | 1 |
| Example 15 | 12.00 | 0.57 | 1.01 | 6.83 | 0.98 | 0.98 | 0.38 | 0.12 | | | Oxalic acid | 49 | 40 | 6 |
| Example 16 | 12.00 | 0.57 | 1.01 | 6.83 | 0.98 | 0.98 | 0.38 | 0.12 | | | Tartaric acid | 40 | 40 | 3.5 |
| Example 17 | 12.00 | 0.57 | 1.01 | 2.24 | 6.54 | | 0.38 | 0.12 | | | Oxalic acid | 85 | 38 | 3.5 |
| Example 18 | 12.00 | 0.82 | 1.45 | 8.14 | | | 0.55 | 0.13 | | | Oxalic acid | 80 | 39 | 3.5 |
| Example 19 | 12.00 | 1.05 | 1.40 | 8.15 | | | 0.70 | 0.13 | | | Oxalic acid | 74 | 40 | 3.5 |
| Example 20 | 12.00 | 0.84 | 2.06 | 6.67 | | | 0.56 | 0.12 | | | Oxalic acid | 106 | 40 | 3.5 |
| Example 21 | 12.00 | 0.27 | 0.95 | 9.64 | | | 0.18 | 0.13 | | | Oxalic acid | 90 | 41 | 3.5 |
| Example 22 | 12.00 | 0.27 | 0.95 | 8.16 | 1.48 | | 0.18 | 0.13 | | | Oxalic acid | 64 | 40 | 3.5 |
| Example 23 | 12.00 | 0.27 | 0.95 | 7.67 | 1.97 | | 0.18 | 0.13 | | | Oxalic acid | 74 | 39 | 3.5 |
| Example 24 | 12.00 | 0.27 | 0.95 | 6.69 | 2.95 | | 0.18 | 0.13 | | | Oxalic acid | 71 | 40 | 3.5 |
| Comparative Example 1 | 12.00 | 0.37 | 1.53 | 4.11 | 3.30 | | 0.81 | 0.14 | | | Oxalic acid | 129 | 20 | 3.5 |
| Comparative Example 2 | 12.00 | 0.37 | 1.53 | 4.11 | 3.30 | | 0.81 | 0.14 | | | Oxalic acid | 31 | 40 | 24 |
| Comparative Example 3 | 12.00 | 0.37 | 1.53 | 4.11 | 3.30 | | 0.81 | 0.14 | | | Oxalic acid | 71 | 40 | 0.1 |
| Comparative Example 4 | 12.00 | 0.37 | 1.53 | 4.11 | 3.30 | | 0.81 | 0.14 | | | Not added | 70 | 41 | 3.5 |
| Comparative Example 5 | 12.00 | 0.37 | 1.53 | 4.11 | 3.30 | | 0.81 | 0.14 | | | Not added | 135 | 20 | 3.5 |
| Comparative Example 6 | 12.00 | 0.37 | 1.53 | 4.11 | 3.30 | | 0.81 | 0.14 | | | Oxalic acid | 40 | 40 | 10 |
| Comparative Example 7 | 12.00 | 0.39 | 1.60 | | 6.97 | 0.77 | 0.63 | 0.17 | | | Oxalic acid | 136 | 22 | 3.5 |
| Comparative Example 8 | 12.00 | 0.39 | 1.60 | | 6.97 | 0.77 | 0.63 | 0.17 | | | Oxalic acid | 65 | 55 | 3.5 |
| Comparative Example 9 | 12.00 | 0.39 | 1.60 | | 6.97 | 0.77 | 0.63 | 0.17 | | | Tartaric acid | 107 | 20 | 3.5 |
| Comparative Example 10 | 12.00 | 1.20 | 0.60 | | 7.80 | | | 1.20 | — | 0.48 | Oxalic acid | 103 | 23 | 3.5 |
| Comparative Example 11 | 12.00 | 0.57 | 1.01 | 6.83 | 0.98 | 0.98 | 0.38 | 0.12 | | | Oxalic acid | 140 | 19 | 3.5 |
| Comparative Example 12 | 12.00 | 0.57 | 1.01 | 6.83 | 0.98 | 0.98 | 0.38 | 0.12 | | | Oxalic acid | 33 | 40 | 24 |
| Comparative Example 13 | 12.00 | 0.57 | 1.01 | 6.83 | 0.98 | 0.98 | 0.38 | 0.12 | | | Oxalic acid | 85 | 40 | 0.1 |
| Comparative Example 14 | 12.00 | 0.57 | 1.01 | 6.83 | 0.98 | 0.98 | 0.38 | 0.12 | | | Not added | 83 | 41 | 3.5 |
| Comparative Example 15 | 12.00 | 0.57 | 1.01 | 6.83 | 0.98 | 0.98 | 0.38 | 0.12 | | | Not added | 142 | 21 | 3.5 |
| Comparative Example 16 | 12.00 | 0.57 | 1.01 | 6.83 | 0.98 | 0.98 | 0.38 | 0.12 | | | Oxalic acid | 42 | 40 | 10 |
| Comparative Example 17 | 12.00 | 0.57 | 1.01 | 2.24 | 6.54 | | 0.38 | 0.12 | | | Oxalic acid | 111 | 20 | 3.5 |
| Comparative Example 18 | 12.00 | 0.82 | 1.45 | 8.14 | | | 0.55 | 0.13 | | | Oxalic acid | 96 | 19 | 3.5 |
| Comparative Example 19 | 12.00 | 1.05 | 1.40 | 8.15 | | | 0.70 | 0.13 | | | Oxalic acid | 86 | 21 | 3.5 |
| Comparative Example 20 | 12.00 | 0.84 | 2.06 | 6.67 | | | 0.56 | 0.12 | | | Oxalic acid | 125 | 20 | 3.5 |
| Comparative Example 21 | 12.00 | 0.27 | 0.95 | 9.64 | | | 0.18 | 0.13 | | | Oxalic acid | 106 | 20 | 3.5 |
| Comparative Example 22 | 12.00 | 0.27 | 0.95 | 8.16 | 1.48 | | 0.18 | 0.13 | | | Oxalic acid | 84 | 22 | 3.5 |
| Comparative Example 23 | 12.00 | 0.27 | 0.95 | 7.67 | 1.97 | | 0.18 | 0.13 | | | Oxalic acid | 91 | 18 | 3.5 |
| Comparative Example 24 | 12.00 | 0.27 | 0.95 | 6.69 | 2.95 | | 0.18 | 0.13 | | | Oxalic acid | 82 | 20 | 3.5 |
| Comparative Example 25 | 12.00 | 0.27 | 0.95 | 6.69 | 2.95 | | 0.18 | 0.13 | | | Oxalic acid | 52 | 39 | 24 |

TABLE 2

| | Ammonia/propylene Molar ratio | Oxygen/propylene Molar ratio | Contact time sec. | Conversion rate of propylene % | AN yield % | ATT strength % |
|---|---|---|---|---|---|---|
| Example 1 | 1.19 | 2.01 | 4.0 | 99.3 | 84.5 | 0.6 |
| Example 2 | 1.20 | 2.06 | 3.8 | 99.2 | 84.5 | 0.2 |
| Example 3 | 1.22 | 1.98 | 3.6 | 99.3 | 84.4 | 0.3 |
| Example 4 | 1.17 | 1.97 | 3.5 | 99.3 | 84.3 | 0.2 |
| Example 5 | 1.20 | 2.02 | 4.2 | 99.3 | 84.3 | 0.2 |
| Example 6 | 1.25 | 2.03 | 3.7 | 99.3 | 84.5 | 0.9 |
| Example 7 | 1.19 | 1.94 | 4.0 | 99.4 | 84.4 | 0.7 |
| Example 8 | 1.18 | 1.98 | 3.9 | 99.3 | 84.4 | 0.2 |
| Example 9 | 1.19 | 2.03 | 4.1 | 99.3 | 84.3 | 0.8 |
| Example 10 | 1.18 | 2.00 | 3.1 | 99.3 | 84.2 | 0.5 |
| Example 11 | 1.20 | 1.99 | 4.1 | 99.3 | 84.5 | 0.7 |
| Example 12 | 1.21 | 2.01 | 3.8 | 99.3 | 84.5 | 0.2 |
| Example 13 | 1.19 | 2.01 | 3.5 | 99.3 | 84.4 | 0.4 |
| Example 14 | 1.18 | 2.05 | 3.5 | 99.2 | 84.3 | 0.2 |
| Example 15 | 1.20 | 2.01 | 4.3 | 99.3 | 84.3 | 0.3 |
| Example 16 | 1.22 | 2.00 | 3.7 | 99.3 | 84.4 | 0.8 |
| Example 17 | 1.22 | 1.98 | 4.0 | 99.3 | 84.3 | 0.2 |
| Example 18 | 1.23 | 1.97 | 4.1 | 99.2 | 84.2 | 0.3 |

TABLE 2-continued

| | Ammonia/ propylene Molar ratio | Oxygen/ propylene Molar ratio | Contact time sec. | Conversion rate of propylene % | AN yield % | ATT strength % |
|---|---|---|---|---|---|---|
| Example 19 | 1.21 | 1.96 | 3.6 | 99.3 | 84.2 | 0.2 |
| Example 20 | 1.24 | 2.04 | 3.8 | 99.3 | 84.1 | 0.4 |
| Example 21 | 1.21 | 1.98 | 3.9 | 99.2 | 84.3 | 0.2 |
| Example 22 | 1.19 | 2.00 | 4.0 | 99.3 | 84.1 | 0.2 |
| Example 23 | 1.18 | 2.06 | 4.0 | 99.3 | 84.2 | 0.3 |
| Example 24 | 1.21 | 2.00 | 4.1 | 99.3 | 84.1 | 0.3 |
| Comparative Example 1 | 1.15 | 2.00 | 4.5 | 99.3 | 84.3 | 1.1 |
| Comparative Example 2 | 1.10 | 1.90 | 5.5 | 99.1 | 82.9 | 0.3 |
| Comparative Example 3 | 1.23 | 2.08 | 3.3 | 99.3 | 84.0 | 0.4 |
| Comparative Example 4 | 1.14 | 1.89 | 4.1 | 99.3 | 83.7 | 0.2 |
| Comparative Example 5 | 1.18 | 2.01 | 4.2 | 99.2 | 83.6 | 0.7 |
| Comparative Example 6 | 1.16 | 1.95 | 4.6 | 99.2 | 83.7 | 0.3 |
| Comparative Example 7 | 1.11 | 1.85 | 4.3 | 99.3 | 84.1 | 1.3 |
| Comparative Example 8 | 1.19 | 2.00 | 3.9 | 99.3 | 83.8 | 0.4 |
| Comparative Example 9 | 1.17 | 1.99 | 4.1 | 99.2 | 84.1 | 2.1 |
| Comparative Example 10 | 1.15 | 2.05 | 3.3 | 99.3 | 83.9 | 1.5 |
| Comparative Example 11 | 1.16 | 2.02 | 4.2 | 99.3 | 84.2 | 1.3 |
| Comparative Example 12 | 1.19 | 2.01 | 5.2 | 99.3 | 82.7 | 0.3 |
| Comparative Example 13 | 1.19 | 2.05 | 4.5 | 99.3 | 84.0 | 0.3 |
| Comparative Example 14 | 1.19 | 2.04 | 4.5 | 99.3 | 83.5 | 0.2 |
| Comparative Example 15 | 1.18 | 2.03 | 4.7 | 99.2 | 83.4 | 0.7 |
| Comparative Example 16 | 1.18 | 2.01 | 4.6 | 99.2 | 83.9 | 0.3 |
| Comparative Example 17 | 1.18 | 2.03 | 4.7 | 99.3 | 84.1 | 1.6 |
| Comparative Example 18 | 1.19 | 2.01 | 4.2 | 99.3 | 84.2 | 1.3 |
| Comparative Example 19 | 1.17 | 2.01 | 4.5 | 99.2 | 84.1 | 1.2 |
| Comparative Example 20 | 1.16 | 2.01 | 4.3 | 99.3 | 84.0 | 2.0 |
| Comparative Example 21 | 1.20 | 2.01 | 4.3 | 99.3 | 84.1 | 1.7 |
| Comparative Example 22 | 1.21 | 2.04 | 4.3 | 99.1 | 83.9 | 1.2 |
| Comparative Example 23 | 1.21 | 2.03 | 4.2 | 99.3 | 84.0 | 1.3 |
| Comparative Example 24 | 1.19 | 2.03 | 4.6 | 99.3 | 84.0 | 1.3 |
| Comparative Example 25 | 1.17 | 2.01 | 4.2 | 99.2 | 82.5 | 0.3 |

As shown in Table 2, in the ammoxidation reaction of propylene using each catalyst produced according to the present embodiment, acrylonitrile can be obtained at a favorable yield. Further, each catalyst produced according to the present embodiment exhibits a favorable attrition strength as a fluidized bed catalyst.

INDUSTRIAL APPLICABILITY

The method for producing an ammoxidation catalyst according to the present invention has industrial applicability as a method for producing a catalyst to be used for ammoxidation reaction of propylene.

The invention claimed is:
1. A method for producing an ammoxidation catalyst, the method comprising:
a step (i) of preparing a starting material slurry comprising molybdenum, bismuth, iron, and a carboxylic acid compound;
a step (ii) of stirring the starting material slurry in a temperature range of 35 to 45° C. for 1 hour to 8 hours, thereby preparing a precursor slurry;
a step of spray-drying the precursor slurry, thereby obtaining a dried particle; and
a step of calcining the dried particle;
wherein the precursor slurry has a viscosity of 1 to 100 cp, and wherein the ammoxidation catalyst has a composition represented by the following formula (1):

$$Mo_{12}Bi_aFe_bX_cY_dZ_eO_f \qquad (1)$$

wherein X represents at least one element selected from the group consisting of nickel, cobalt, magnesium, calcium, zinc, strontium, and barium; Y represents at least one element selected from the group consisting of cerium, chromium, lanthanum, neodymium, yttrium, praseodymium, samarium, aluminum, gallium, and indium; Z represents at least one element selected from the group consisting of potassium, rubidium, and cesium; provided that a proportion of cobalt is 20 atomic % or more and/or a proportion of magnesium is 20 atomic % or less in the element X; a, b, c, d, and e satisfy $0.1 \leq a \leq 2.0$, $0.1 \leq b \leq 3.0$, $0.1 \leq c \leq 10.0$, $0.1 \leq d \leq 3.0$ and $0.01 \leq e \leq 2.0$, respectively; and f represents a number of oxygen atoms needed to satisfy atomic valence requirements of other elements present therein.

2. The method for producing the ammoxidation catalyst according to claim 1, wherein a content of the carboxylic acid compound in the precursor slurry is 0.01 to 0.10 mol equivalents based on a sum of metal elements constituting the ammoxidation catalyst.

3. A method for producing acrylonitrile by reacting propylene, molecular oxygen, and ammonia, wherein the ammoxidation catalyst produced by the method according to claim 1 is used.

* * * * *